United States Patent [19]

Fortin

[11] Patent Number: 5,485,092
[45] Date of Patent: Jan. 16, 1996

[54] METHOD AND DEVICE FOR ELECTROSTATICALLY INVESTIGATING SURFACE AND SUB-SURFACE STRUCTURES

[76] Inventor: Gabriel Fortin, 495, chemin de la cote Ste-Catherine, Outrement, Québec, Canada, H2V 2B7

[21] Appl. No.: 190,046

[22] PCT Filed: Aug. 1, 1991

[86] PCT No.: PCT/CA91/00270

§ 371 Date: Jan. 31, 1994

§ 102(e) Date: Jan. 31, 1994

[87] PCT Pub. No.: WO93/03403

PCT Pub. Date: Feb. 18, 1993

[51] Int. Cl.⁶ .................................................. G01N 27/60
[52] U.S. Cl. ...................... 324/457; 324/663; 324/671; 324/672
[58] Field of Search .................................. 324/457, 458, 324/663, 671, 672, 678, 679, 686, 687, 690

[56] References Cited

U.S. PATENT DOCUMENTS

| | | | |
|---|---|---|---|
| 4,065,715 | 12/1977 | Jaffe et al. | 324/678 |
| 4,099,118 | 7/1978 | Franklin et al. | 324/671 |
| 4,145,619 | 3/1979 | Tseng | 307/118 |
| 4,208,695 | 6/1980 | Noda et al. | 361/181 |
| 4,310,797 | 1/1982 | Butler | 324/228 |
| 4,464,622 | 8/1984 | Franklin | 324/67 |
| 4,686,454 | 8/1987 | Pecukonis | 324/67 |
| 4,767,940 | 8/1988 | Tuttle | 307/116 |
| 4,992,741 | 2/1991 | Douglas et al. | 324/671 |
| 5,315,884 | 5/1994 | Kronberg | 324/671 X |

FOREIGN PATENT DOCUMENTS

| | | |
|---|---|---|
| 963553 | 2/1975 | Canada . |
| 0398728 | 11/1990 | European Pat. Off. . |
| 3743180 | 7/1988 | Germany . |
| 1600261 | 10/1981 | United Kingdom . |
| 2188432 | 9/1987 | United Kingdom . |

*Primary Examiner*—Kenneth A. Wieder
*Assistant Examiner*—Glenn W. Brown
*Attorney, Agent, or Firm*—Cushman, Darby & Cushman

[57] ABSTRACT

An electrostatic sensing device for investigating a surface and/or sub-surface structure comprises a central and square electrically conductive sensor plate, and four side electrically conductive elongated and rectangular sensor plates connected together and each disposed adjacent and parallel to one edge of the central plate. The arrangement of sensor plates is applied to the surface, and the central and sensor plates are then electrically charged at different rates, the charging rate of the central plate being affected by the permittivity of the investigated structure to electric field. A differential amplifier amplifies the difference between the voltages on the central and side plates as these plates charge, and a peak detector detects the highest amplitude of this amplified voltage difference and displays it on a voltmeter. As the permittivity of the structure under investigation is function of at least one characteristic thereof, and as the voltage difference is affected by the charging rates of the central and side plates themselves affected by the permittivity to electric field, the output signal from the peak detector is indicative of this characteristic of the inspected structure.

13 Claims, 3 Drawing Sheets

FIG. 5

METHOD AND DEVICE FOR ELECTROSTATICALLY INVESTIGATING SURFACE AND SUB-SURFACE STRUCTURES

BACKGROUND OF THE INVENTION

1. Field of the Invention

The present invention relates to a method and device capable of electrostatically investigating a surface and/or sub-surface structure. In particular but not exclusively, the method and device in accordance with the present invention are capable of sensing variations in the composition and density of material structures, and the presence of an internal mass in a building structure.

2. Brief Description the Prior Art:

A known method, capable of carrying out scientific measurements of dielectric constants in wood and materials containing wood, uses a pair of electrically conductive plates of the same dimensions applied on opposite sides of the wooden sample to fill all the space between the plates with this sample. An alternating current is then applied to the capacitor formed by the two plates and the sample. Theoretically, the capacitor may be applied to several points of a piece of wood to detect changes in the dielectric constant thereof. However, this procedure presents numerous disadvantages:

- the plates along with the supply leads have to be applied to opposite sides of the wooden sample, which is often impracticable;
- filling the space between the two plates with the sample is impossible when an internal member of an already erected building structure should be inspected;
- electrocution hazards exist as conductive material is generally present in the structures under investigation; and
- the measurements must be compared to known values, which requires calibration.

An adaptation of the above method is the application of a pair of capacitive plates on the same face of a tested material. As the intensity of the electric field is inversely proportional to the square of the distance between electrically conductive plates charged with opposite polarities, the sensitivity of such capacitive sensors and the applications thereof are severely restricted.

An "electronic wall stud sensor" is described in U.S. Pat. No. 4,099,118 granted to Franklin et al. on Jul. 4, 1978. This sensor includes two sets of electrically conductive plates applied on the surface of a wall to be investigated. The plates of the two sets are charged at different rates and the sensor measures the difference in the time for the plate sets to reach a given voltage threshold, this time difference varying with the density of the sub-surface density. Although the stud sensor of Franklin et al. may be effective in some applications, it however presents the following drawbacks:

- the stud sensor requires calibration to be operational;
- if the initial calibration is made over a point to be detected, that is a point of high density corresponding to the position of a stud, the stud sensor will not detect the studs; it will not detect the points of high density as long as the calibration is made over a point of low density through trial and error;
- after successful calibration, the stud sensor will indicate points on the wall where the density is higher than that of the point of the last calibration;
- frequent calibration may be necessary;
- the stud sensor will not produce meaningful readings or may give misleading indications in the presence of thicker surface material, as is often the case in wood lath and plaster walls and in gypsum board walls and ceilings where thick layers of plaster are present to level off joints;
- it cannot operate meaningfully on wooden board or plank finish, because of the thickness of such a finish and the generally significant variations in density from one board or plank to the other;
- it will not operate either in the presence of electrically conductive fasteners used in walls and ceilings, and more generally in the case of wood board finish floors;
- within its range of sensitivity, it will signal the presence of electrically conductive materials, without depth discrimination;
- it presents a low resolution in the detection of conductors.

U.S. Pat. No. 4,992,741 granted to Douglas et al. on Feb. 12, 1991, proposes a device for detecting objects behind a wall. This detecting device comprises a plurality of capacitor plates at spaced intervals and a circuit for sensing alterations in the dielectric constant of a region of the surface being inspected close to each capacitor plate. Display elements are respectively associated to the capacitor plates to display the signals detected through these plates and image the object being detected. Although this detecting device may be efficient in some applications, its sensitivity is limited since, as discussed hereinabove, the intensity of the electric field is inversely proportional to the square of the distance between the plates charged with opposite polarities. The device of Douglas et al. is also susceptible of performing erroneous readings due to the user's position with respect to the detecting device. Finally, it is complex and expensive.

OBJECT OF THE INVENTION

The object of the-present invention is to provide a sensing device comprising at least two electrically conductive plates placed in the proximity of a surface and or sub-surface structure to be inspected. These plates are then electrically charged at different rates. In accordance with the present invention, the sensing device detects the difference between the voltages on the plates as they charge, in order to eliminate the above discussed drawbacks of the prior art. This voltage difference is affected by at least one Characteristic of the structure under investigation, such as its density, its composition, its internal configuration, etc. and is therefore indicative of this characteristic.

SUMMARY OF THE INVENTION

In accordance with the present invention, there is provided an electrostatic sensing device for investigating a surface and/or sub-surface structure presenting a permittivity to electric field which is a function of at least one characteristic of that structure. The sensing device comprises (a) at least one first electrically conductive sensor plate that can be placed in the proximity of the structure under investigation, (b) at least one second electrically conductive sensor plate that can be placed in the proximity of the investigated structure and adjacent the first plate without contacting it, and (c) means for electrically charging the first and second plates at different rates, the charging rate of at least one of the first and second plates being affected by the permittivity of the structure to the electric field produced by the plates being charged. A detecting and generating circuit detects a difference between respective electric voltages on the first and second plates as these plates charge, and generates an output signal representative of the amplitude of this voltage difference which is affected by the charging rates of the first and second plates themselves affected by the permittivity of the structure to electric field. As the output signal is a function of this permittivity, it is therefore indicative of said at least one characteristic of the structure under investigation.

In accordance with a preferred embodiment of the electrostatic sensing device of the invention, the detecting and generating circuit comprises (a) a differential amplifier having a first input connected to the first plate and a second input connected to the second plate for amplifying the difference between the voltages on the first and second plates, (b) a peak detector for detecting the highest amplitude of the amplified voltage difference from the differential amplifier and for generating the output signal in relation to this highest amplitude, and. (c) a voltmeter for displaying the amplitude of the output signal from the peak detector.

According to other preferred embodiments of the present invention, the sensing device comprises a plurality of electrically conductive second sensor plates electrically connected together;

the first plate and the plurality of second plates are mounted on a common plate support;

the first plate is a central electrically conductive sensor plate presenting two opposite edges, and the plurality of second plates comprises two side electrically conductive sensor plates mounted adjacent the two opposite edges of the central plate, respectively;

the first plate is a central electrically conductive sensor plate formed with three edges, and the plurality of second plates comprises three side electrically conductive sensor plates mounted adjacent the three edges of the central plate, respectively;

the first plate comprises a central electrically conductive sensor plate formed with four edges, and the plurality of second plates comprises four side electrically conductive sensor plates mounted adjacent the four edges of the central plate, respectively;

(a) the central and side plates are coplanar, or (b) the central plate is planar and each side plate defines an acute angle with the plane of the central plate to orient one face of the side plate toward a zone located beneath the central plate.

(a) the central plate is square, (b) the edges of the central plate are straight and have a given length, (c) the side plates are rectangular and elongated, and have a length equal to the length of the edges of the central plate, and (d) each side plate is parallel to the corresponding edge of the central plate;

when the sensing device comprises four side plates, a switching means may be provided to disconnect at least one of the four side plates from the three other ones.

The electrostatic sensing device preferably comprises a switching member for periodically discharging the sensor plates whereby they can be charged again by the plate charging means to allow the detecting and generating circuit to generate another output signal indicative of said at least one characteristic.

The present invention also relates to a method of electrostatically investigating a surface and/or sub-surface structure presenting a permittivity to electric field which is a function of at least one characteristic of that structure, comprising the steps of (a) placing at least one first electrically conductive sensor plate in the proximity of the structure under investigation, (b) placing at least one second electrically conductive sensor plate in the proximity of the investigated structure and adjacent the first plate without contacting it, and (c) electrically charging the first and second plates at different rates, the charging rate of at least one of the first and second plates being affected by the permittivity of the structure to the electric field produced by the plates being charged. A difference between respective electric voltages on the first and second plates is detected as these plates change, and an output signal representative of the amplitude of this voltage difference is generated. As the voltage difference is affected by the charging rates of the first and second plates themselves affected by the permittivity of the structure to electric field, the output signal is a function of this permittivity and is therefore indicative of said at least one characteristic of the structure under investigation.

Preferably, the voltage difference detecting step comprises amplifying the difference between the voltages on the first and second plates, the output signal generating step comprises detecting the highest amplitude of the amplified voltage difference and generating the output signal in relation to this highest amplitude, and the electrostatically investigating method further comprises the step of displaying the amplitude of the output signal generated in relation to the highest amplitude of the amplified voltage difference.

The electrostatically investigating method may further comprise the step of periodically discharging the first and second sensor plates whereby they can be charged again to enable generation of another output signal indicative of said at least one characteristic of the structure under investigation.

The objects, advantages and other features of the present invention will become more apparent upon reading of the following non restrictive description of preferred embodiments thereof, given by way of example only with reference to the accompanying drawings.

DETAILED DESCRIPTION OF THE PREFERRED EMBODIMENTS

Figure 1:
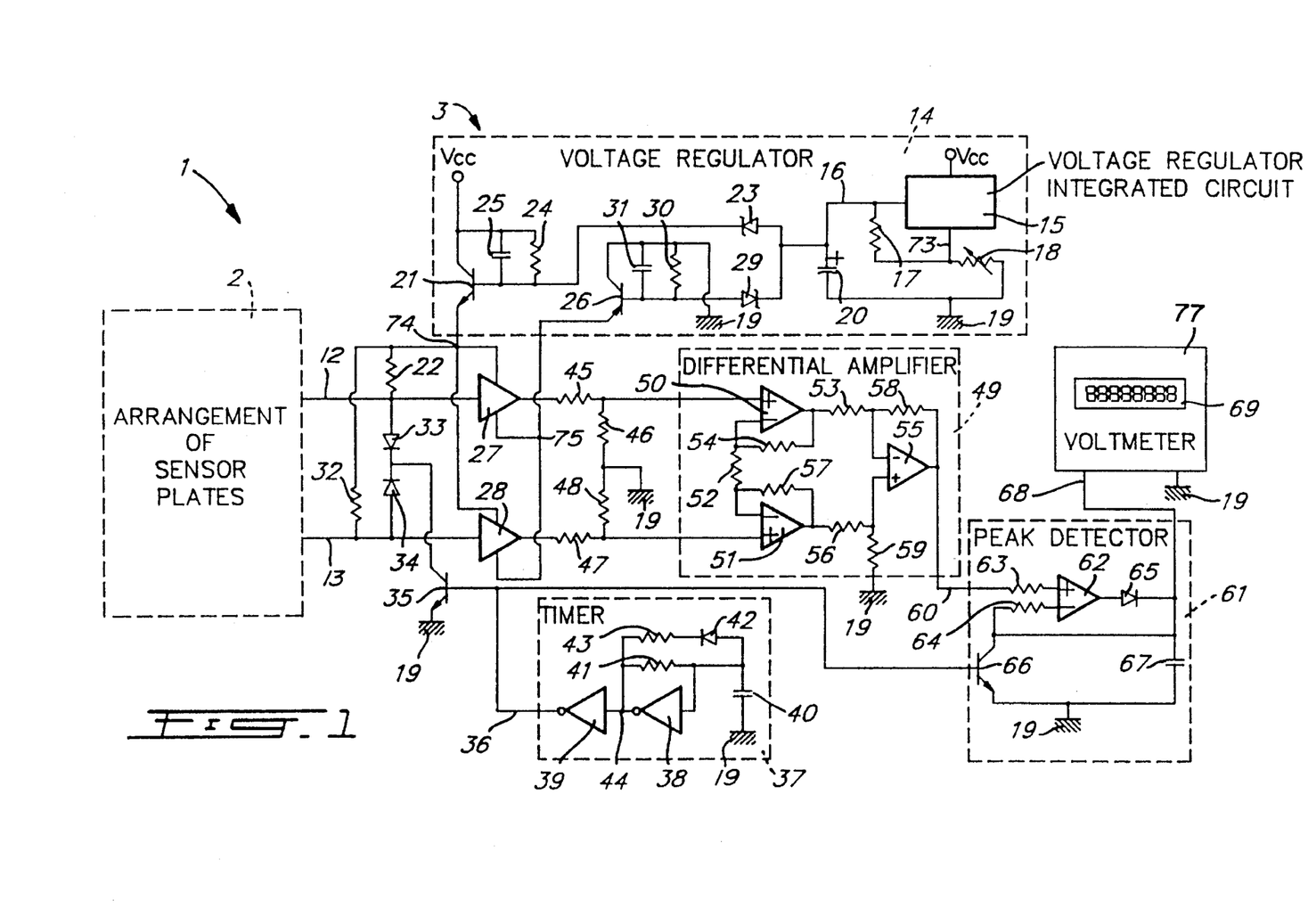
FIG. 1 is a schematic illustration of an electrostatic sensing device in accordance with the present invention, including an arrangement of sensor plates.

As illustrated in FIG. 1, the electrostatic sensing device according to the invention, generally identified by the reference numeral 1, comprises an arrangement 2 of sensor plates and an electronic circuit 3 including (a) a voltage regulator 14, (b) a timer 37, (c) a differential amplifier 49, (d) a peak detector 61, and (e) a voltmeter 77.

Figure 2:
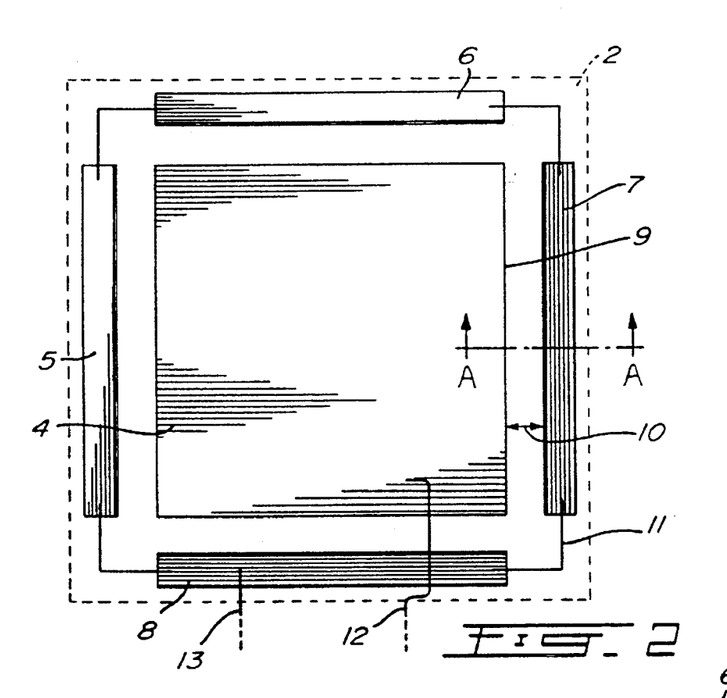
FIG. 2 illustrates a first embodiment of the arrangement of sensor plates of the sensing device of FIG. 1, including a central plate and four side plates.

The first arrangement 2 of sensor plates, as shown in FIG. 2, comprises an electrically conductive central plate 4 and four electrically conductive side plates 5–8. The five plates 4–8 can be coplanar (see central plate 4 and side plate 7' (dashed lines) in FIG. 4 ). In the illustrated example, the central plate 4 is square while the side plates 5–8 are elongated and rectangular. Each side plate 5, 6, 7 or 8 has the same length as the adjacent edge such as 9 of the central plate 4, it is parallel to this edge and is spaced apart therefrom by a distance 10.

The adjacent ends of each pair of successive side plates 5–8 are electrically connected together through a conductor such as 11 whereby the side plates 5–8 define an electrical loop surrounding the central sensor plate 4. This central plate 4 is electrically connected to the electronic circuit 3 (FIG. 1) through an electric wire 12 while the loop defined by the interconnected side plates 5–8 is connected to this electronic circuit 3 through another electric wire 13.

The arrangement 2 of sensor plates will be described in further detail in the following description.

Referring back to FIG. 1, the voltage regulator 14 comprises a voltage regulator integrated circuit 15 supplied with a direct current (DC) supply voltage Vcc. The integrate$_d$ circuit 15 produces on its output 16 a regulated reference DC voltage having an amplitude which is function of the resistance value of a potentiometer 18 forming a voltage divider with a resistor 17. This resistor 17 is connected between the output 16 and another pin 73 of the integrated circuit 15, and the potentiometer 18 is interposed between the pin 73 and the ground 19 of the electronic circuit 3. A capacitor 20, connected between the output 16 and the ground 19, stabilizes the output reference DC voltage. The operation of voltage regulator integrated circuits such as 15 are well known in the art and accordingly will not be fully described in the present specification. For example, the integrated circuit 15 can be constituted by the voltage regulator (catalogue number TL783C) commercialized by the company Texas Instruments.

The voltage regulator 14 also comprises an NPN transistor 21. The transistor 21 has its collector supplied by the supply DC voltage Vcc and its emitter connected to (a) the positive supply terminals of buffers 27 and 28, (b) the input of the buffer 27 through a resistor 22, (c) the input of the buffer 28 through a resistor 32, (d) the central plate 4 (FIG. 2) through the resistor 22 and the electric wire 12, and (e) the side plates 5–8 (FIG. 2) through the resistor 32 and the wire 13. The base of transistor 21 is Connected to the output 16 of the integrated circuit 15 through a Zener diode 23, having its cathode connected to the base of transistor 21 and its anode connected to the output 16. A resistor 24 is connected in parallel with a capacitor 25 between the collector and the base of the transistor 21.

The regulator 14 further comprises a PNP transistor 26 having its collector grounded, its emitter connected to the negative supply terminals of the buffers 27 and 28, and its base connected to the output 16 of the integrated circuit 15 through a Zener diode 29, having its cathode connected to the output 16 and its anode connected to the base of transistor 26. A resistor 30 is connected in parallel with a capacitor 31 between the collector and the base of the transistor 26.

The electronic circuit 3 further comprises a diode 33 having its anode connected to the central plate 4 through the wire 12, and another diode 34 having its anode connected to the side plates 5–8 through the wire 13. The cathodes of these two diodes 33 and 34 are connected to the collector of an NPN transistor 35. This transistor 35 has its emitter grounded and its base connected to the output 36 of the timer 37.

In the embodiment of FIG. 1, the timer 37 comprises a pair of serially interconnected inverters 38 and 39, a capacitor 40 interposed between the input of the inverter 38 and the ground 19, a resistor 41 interconnecting the input of the inverter 38 and the junction 44 between the output of the inverter 38 and the input of the inverter 39. As can be seen, the output of the inverter 39 constitutes the output 36 of the timer 37. A resistor 43 is connected in series with a diode 42 between the junction 44 and the input of the inverter 38, with the anode of the diode 42 connected to the input of the inverter 38 and the cathode of this diode connected to the adjacent terminal of the resistor 43.

A first voltage divider is formed by resistors 45 and 46 connected in series between the output of the buffer 27 and the ground 19 while a second voltage divider is formed by resistors 47 and 48 serially interconnected between the output of the buffer 28 and the ground 19.

The differential amplifier 49 has a high input impedance and includes a first operational amplifier 50 with a non-inverting input connected to the junction between the resistors 45 and 46, and with an inverting input connected to the inverting input of another operational amplifier 51 through a resistor 52. The non-inverting input of the operational amplifier 51 is connected to the junction between the resistors 47 and 48. A resistor 54 is connected between the inverting input of the operational amplifier 50 while another resistor 53 is interposed between the output of the amplifier 50 and the inverting input of a third operational amplifier 55. The differential amplifier 49 further-comprises a resistor 57 interposed between the output and the inverting input of the operational amplifier 51 and a resistor 56 interconnects the output of the amplifier 51 and the non-inverting input of the third operational amplifier 55. A resistor 58 interconnects the output and the inverting input of the operational amplifier 55. Finally, a resistor 59 is connected between the ground 19 and the non-inverting input of the amplifier 55. As Shown in FIG. 1, the output of the operational amplifier 55 constitutes the output 60 of the differential amplifier 49.

In the differential amplifier 49, the resistors 53, 54, 56, 57, 58 and 59 are semi-precision resistors of the same resistance, the gain of the differential amplifier 49 being adjusted by the resistance value of the resistor 52. The resistor 52 can be formed by a potentiometer to make the gain of differential amplifier 49 adjustable.

The peak detector 61 includes an operational amplifier 62 connected in a voltage-comparator configuration. This amplifier 62 has a non-inverting input connected to the output 60 of the differential amplifier 49 through a resistor 63, and an output connected to the input 68 of the voltmeter 77 through a diode 65 having its anode connected to the output of the amplifier 62 and its cathode connected to the voltmeter input 68. The inverting input of the operational amplifier 62 is connected through a resistor 64 to the cathode of the diode 65 and to the collector of an NPN transistor 66 having its emitter grounded and its base connected to the output 36 of the timer 37. A capacitor 67 is interposed between the cathode of the diode 65 and the ground 19. Accordingly, the capacitor 67 is interposed between the collector and the emitter of the transistor 66.

As can be seen in FIG. 1, the voltmeter 77 is connected to the ground 19 of the electronic circuit 3 and includes an assembly 69 of seven-segment display units. The voltmeter 4 can be replaced by numerous other devices such as light-emitting diodes, bar graphs, sound frequency generators, analog-to-digital converters, etc. which are also capable of signaling the level of the voltage peak detected by the detector 61.

The structure of the sensing device 1 having been described in detail in the foregoing description with reference to FIGS. 1 and 2, its operation will now be explained.

In operation, the arrangement 2 of sensor plates is first applied to a surface of a structure to be investigated. The potentiometer 18 (FIG. 1) is then operated to adjust the ratio of the voltage divider 17–18 and thereby select the level of the reference DC voltage on the output 16. This adjustment enables selection of the level of the operating voltage of the sensing device 1, taking into consideration the particular application and the level of sensitivity required.

The reference DC voltage on the output 16 of the integrated circuit 15 is supplied to the base of the transistor 21 through the Zener diode 23 and establishes a biasing voltage on the base of the transistor 26 through the Zener diode 29. This reference voltage accordingly controls the transistors 21 and 26 to determine the level of the operating voltage at the emitter of the transistor 21 (point 74). It also adjusts in function of the operating voltage at point 74 the amplitude of the DC voltage between points 74 and 75 (between the emitters of the transistors 21 and 26), supplying the buffers 27 and 28.

As can be appreciated by one skilled in the art, the timer 37 is of conventional structure, and detailed description or its operation is believed unnecessary. It produces on its output 36 a periodic square wave. During each period, this square wave comprises a low level signal portion applied to the base of transistor 35 to switch it off. The duration of the low level signal portion is determined by the time constant RC of the resistor 41 and capacitor 40. The DC voltage at point 74 then charges the Central plate 4 through the resistor 22 and the electric wire 12, and the side plates 5–8 through the resistor 32 and the wire 13.

Figure 5:
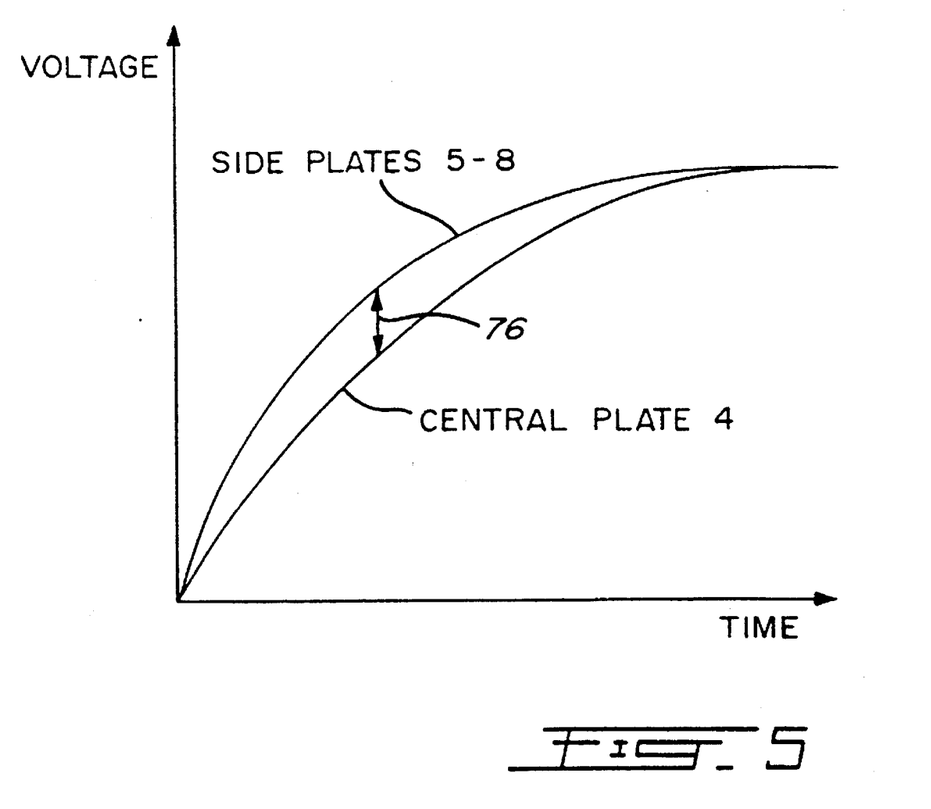
FIG. 5 is a graph showing the evolution of the difference in amplitude between the voltages on the central and side plates as these sensor plates charge.

The resistance values of the resistors 22 and 32 are selected to charge the side plates 5–8 at a slightly higher rate than the central plate 4. During the charging of the sensor plates of the arrangement 2, the voltage on the interconnected side plates 5–8 is slightly higher than the voltage on the central plate 4. FIG. 5 shows the evolution of the voltages on the side plates 5–8 and on the central plate 4 as the sensor plates charge.

The voltage difference 76 (FIG. 5) is affected by the permittivity of the investigated surface and/or sub-surface structure to electric field itself affected by at least one characteristic of that structure, such as the density, composition, internal configuration, etc. Indeed, as the different plates 4–8 charge, the electric charge on the side plates 5–8 will produce an electric field which oppose to that produced by the electric charge on the central plate 4. This will reduce the charging rate of the central plate as a function of the permittivity of the investigated structure in which the electric field propagates, which permittivity is itself related to at least one of the above mentioned structural characteristics. This will also increase the amplitude of the voltage difference 76 in relation to the reduction of the charging rate of the central plate 4. As the voltage difference 76 is affected by the charging rate of the central plate 4 itself affected by the permittivity to electric-field of the structure under investigation, this voltage difference is a function of this permittivity and therefore of the said at least one structural characteristic. This will be further elaborated hereinafter.

The resistance of the resistors 22 and 32 can be adjusted in factory at given values. They can also be constituted by potentiometers to make them adjustable. A wide range of adjustments of the charging rates of the central and side-plates-and of the operating voltage are possible to take into consideration the dimensions and configuration of the sensor plates, the particular application, etc.

At the end of each period, the square wave on the output 36 of the timer 37 comprises a high level signal portion applied to the base of the transistor 35 to switch it on and discharge to the ground 19 the sensor plates 4–8 through the diodes 33 and 34 and the junction collector-emitter of the transistor 35. The diode 42 and the resistor 43 of the timer 37 causes a very fast discharge of the capacitor 40 during which the output signal of the timer 37 is high and switches the transistor 35 on. In the preferred embodiment, the high level signal portion of each wave period has a duration of 0.2 msec.

As the central 4 and side 5–8 plates charge, the voltage on the central plate 4 is applied to the non-inverting input of the operational amplifier 50 through the wire 12, the voltage-follower buffer 27, and the voltage divider 45–46. Regarding the voltage on the side plates 5–8, it is applied to the non-inverting input of the operational amplifier 51 through the electric wire 13, the voltage-follower buffer 28, and the voltage divider 47–48. Obviously, the buffers 27 and 28 prevent the charging circuit 14;22;32;12;13 from being loaded by the electronic circuit 3 of the sensing device 1.

The voltage dividers 45;46 and 47;48 enable high voltage operation of the sensor plate arrangement 2. Indeed, these dividers 45;46 and 47;48 reduces the amplitude of such a high voltage to a level acceptable by the differential amplifier 49, when high voltage operation of the sensing device 1 is selected through the potentiometer 18. Of course, the resistance values of the resistors 45–48 are selected or are adjustable to supply the operational amplifiers 50 and 51 with voltages of acceptable levels for all the amplitudes of operating voltage that can be supplied by the voltage regulator 14 at point 74 and selected through adjustment of the potentiometer 18.

The differential amplifier 49, of which the gain is selected by the resistance value of the resistor 52, amplifies the difference between the voltages applied to the non-inverting inputs of the operational amplifiers 50 and 51. Accordingly, the differential amplifier 49 produces on its output 60 an amplified voltage difference which is representative of the amplitude of the voltage difference 76 (see FIG. 5) as the central and side sensor plates charge.

The amplified voltage difference at the output 60 of the differential amplifier 49 is applied to the peak detector 61. As during charging of the sensor plates 4–8 the signal on the output 36 of the timer 37 is low, the junction collector-emitter of the transistor 66 is non conductive. Accordingly, the operational amplifier 62, connected in a voltage-comparator configuration, charges the capacitor 67 through the diode 65 to the voltage amplitude received on its non-inverting input. As the transistor 66 is switched off by the low level signal portion the output 36 of the timer 37 and as the diode 65 is interposed between the capacitor 67 and the output of the amplifier 62, one can appreciate that the voltage across the capacitor 67 is representative of the highest amplitude of the voltage having appeared on the output 60 and accordingly the highest voltage difference 76 having appeared between the voltages on the central plate 4 and on the side plates 5–8 during the corresponding period of the square wave on the output 36 of the timer 37.

The voltage across the capacitor 67 is applied to the input 68 of the voltmeter 4 and its amplitude is indicated on the display 69. One can appreciate that the displayed voltage amplitude, which is representative of the highest voltage difference 76 as discussed hereinabove, provides the operator with indications about the characteristics of the structure under investigation.

At the end of each period of the square wave on the output 36 of the timer 37, the high level signal portion will switch the transistor 66 on to discharge the capacitor 67 and thereby reset the peak detector 61 in view of the next measurement. The capacitor 67 and the sensor plates of the arrangement 2 are therefore discharged simultaneously to reset the sensing device 1 which is then ready to carry out another sensor plate charging operation in view of performing another measurement.

The arrangement of sensor plates 2 illustrated in FIG. 2 comprises a square central plate 4. This is not compulsory but selecting the central sensor plate 4 square will improve the precision of the device 1 in locating floor joists or electrically conductive fixing nails and/or screws driven at the sub-floor level in a wood-board finish floor.

The dimensions of the central plate 4 may vary considerably according to the characteristic to be detected in the structure under investigation. Experiments were conducted (a) with a central plate 4 as narrow as 5 mm and with an operating voltage of 12 volts to measure changes in density at the surface of wood boards, and (b) with a central plate 4 as wide as 20 cm and with an operating voltage 80 volts to locate joists in floors made of heavy wood pieces-or made thicker as a result of resurfacing on top of an existing floor. These experiments gave good results and demonstrated that the dimensions of the central plate 4 may widely vary in accordance with the intended application.

When the embodiment of FIG. 2 is used to precisely locate floor joists and/or sub-floor nails and/or screws when they are situated in the center of the central plate 4, the latter plate is advantageously square with edges 120 mm long, the rectangular side plates 5-8 are 120 mm long and 20 mm wide, and the operating voltage is 40 volt. This embodiment is capable of locating joists in a floor made of 20 mm thick wood board sub-flooring covered by 20 mm thick by 60 mm wide hardwood floor board finish. Sensor plates 4-8 of larger dimensions can however be used with adequate voltage, when required by the intended application. The thickness of the sensor plates 4-8 is not a critical factor since, as well known in the art, the electric charge concentrates at the surface of a conductor; in practical terms, however, sensor plates 4-8 as thin as 0.1 mm will properly conduct the charge while minimizing the losses of electric field through the edges of the sensor plates.

In the sensor plate arrangement 2 of FIG. 2, the distance 10 between one edge of the central plate 4 and the adjacent edge of the corresponding side plate 5, 6, 7 or 8 is either permanently set or adjustable through a suitable mechanism (not shown). Experiments were conducted with distances 10 varying from 2 mm for surface density measurement, to 30 mm for locating deep joists of a wood floor. A larger distance 10 minimizes the sensitivity of the sensing device 1 to the structure close to the top surface of the floor to which one face of the arrangement 2 is applied. However, the distance 10 must not overstep a practical unit for given dimensions of the central plate 4 and a given operating voltage level. Such limits may be extended by orienting the side plates 5-8 at an angle 70 (see FIG. 4) with respect to the plane of the central plate 4. While the distance 10 deviates the electric field, as evidenced by the loss of sensitivity to structure closer to the surface, a set or adjustable angle 70 concentrates or focuses the remaining electric field emanating from the central plate 4 deeper in the wood floor structure; this is evidenced by the possibility of precisely locating target elements such as the nails and/of screws fixing the sub-floor to the joists. In the embodiment of the sensor plate arrangement 2 illustrated in FIGS. 2 and 4, the distance 10 can be set at 25 mm and the angle 70 is set at 20°. These values are adequate to locate the joists and sub-floor nails and/or screws in the above-described wood-board finish floor.

Figures 3, 4:
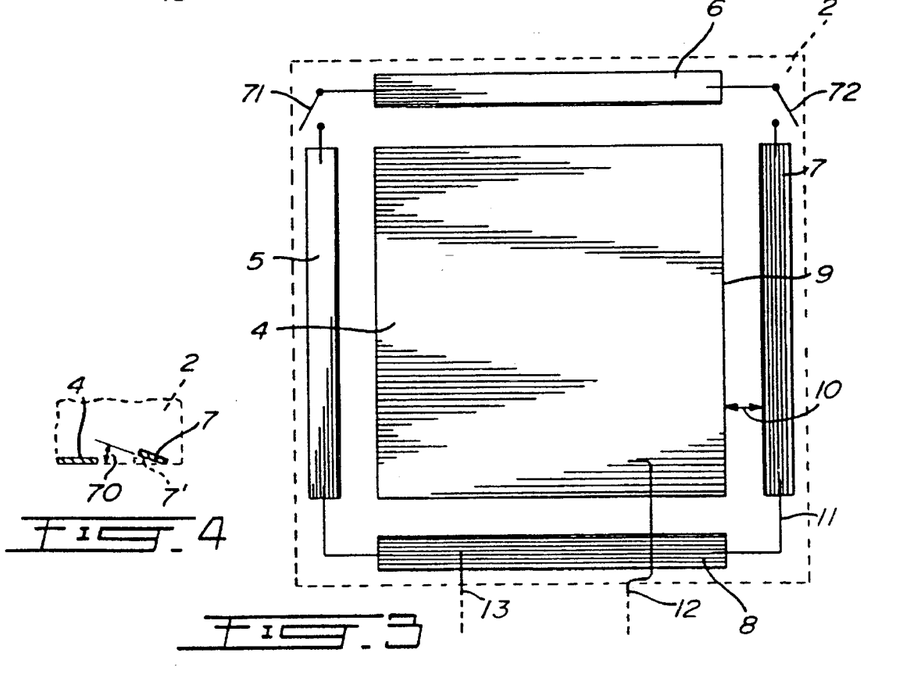
FIG. 3 illustrates a second embodiment of the arrangement of sensor plates of the sensing device of FIG. 1, including a central plate and three or four side plates.
FIG. 4 is a cross sectional view of the arrangement of sensor plates of FIG. 2, taken along line A—A.

In the arrangement 2 of sensor plates illustrated in FIG. 3, the electric conductor 11 interconnecting the adjacent ends of the side plates 5 and 6, and the electric conductor 11 interconnecting the adjacent ends of the side plates 6 and 7 are replaced by electric switches 71 and 72, respectively, to enable selective connection of the side plates 5-8 to form a loop as shown in FIG. 2, or in series as required in certain applications. It will be readily understood from the foregoing description that the configuration of the arrangement 2 of sensor plates should be adjusted as a function of better focusing the electric field in the area of interest; in which where are located target elements such as the joists or beams of a wood floor, electrically conductive elements such as nails and/or screws in delimited floor areas, for example over joists or between joists, as desired. Although the arrangement 2 of sensor plates shown in FIG. 3 can be switched from one configuration to the other, the distance 10 between each edge of the central plate 4 and the adjacent edge of the corresponding side plate 5, 6, 7 or 8, and the angle 70 defined by each side plate 5-8 with the plane of the central plate 4, can still be set or adjusted according to the intended application.

When the switches 71 and 72 are open, the downward sensitivity of the sensing device 1 is nearly doubled, but precise location of small conductive target elements is improved when the switches 71 and 72 are closed. The switches 71 and 72 therefore permit detailed analysis of the structure of a wood-board finish floor, including precise location of structural and fixing elements, pipes, wires in any state of loading or shielding, expansion tanks and any other elements that should be exactly localized prior to repairing or for any other purpose.

Where high precision location of conductive elements under a surface is not required, side plate 6 can be removed and side plate S replaced by a conductor interconnecting the side plates 5 and 7. However, the adjustable features 10 and 70 are retained. This configuration of the arrangement 2 provides for additional flexibility in the geometry of the central plate 4 and a wider range of downward sensitivity in locating embedded target elements. As indicated in the foregoing description, a central plate 4 as narrow as 5 mm with a distance of 2 mm will indicate small variations in the identity of a surface of wood (structure under investigation) or of other surfaces made of similar material structure. Larger central plate 4, distance 10 and operating voltage level will enable detection of variations of density in larger pieces of material (structure under investigation) attributable to natural variations in fibrous structure, faults, decay, etc. that must be identified to control quality and classify materials, and to assess the structural soundness of elements of building structures.

Extensive experimentation with the sensing device I indicates that the central plate 4 and the side plates 5-8, in the arrangement 2 of FIG. 2, are repeatedly charged with opposing electric charges in a moving electrostatic condition; as distance 10 and angle 70, as well as the dimensions and the geometry of the sensor plates 4–8 vary, the electric field generated by the side plates 5–8, more or less circumscribes the electric field generated by the central plate 4, thus forcing all or most of the electric field vectors produced by the central plate 4 downwardly into the wood Structure, where the local permittivity to the electric field restricts in similar proportion dispersion of the electric field produced by the central plate 4, and the charging rate of that plate 4.

The electronic circuit 3, to which the arrangement 2 of sensor plates is connected, enables a broad range of configuration for the sensor plates, of dimensions and geometry of these sensor plates, of distances 10, and of angles 70, which the voltage regulator 14 provides a wide range of electric field intensity, all of which, acting together, as required, enable a wide range of applications, of which the above-described applications are only non limitative illustrations. The calibration of the sensing device may be set in factory, or may be adjustable within a given range (through the above mentioned adjustable elements) in which the device 1 is readily operational. With the sensing device in accordance with the present invention, a meaningful reading is obtained each time it is applied locally.

By applying the device 1 sequentially to different points of the surface of the structure under investigation, local permittivity to electric field is expressed for each point in terms of the difference between the charging rate of the side plate 5–8 and the charging rate of the central plate 4 to provide the operator with indications of the nature of the surface and of the sub-surface. The foregoing explanations apply to all the configurations of sensor plates.

The flexibility in design and easy operation of the sensing device according to the present invention provides for operation thereof by a human operator or machine operator; in the latter case, a data acquisition and control system would automatically adjust, for instance, the potentiometer 18, the resistors 22 and 32, the voltage dividers 45–46 and 47–48, the resistor 52, etc. a single device 1 or of an array of devices 1, as required by the intended application.

Of course, the housing (not shown) of the sensing device 1 can be easily adapted to the application and the operating conditions. In the above-described preferred embodiment, designed for investigating wood-board finish floor structures, the arrangement 2 of sensor plates can be mounted on a thin plate made of a material having a low dielectric constant such as teflon. This plate can be easily fitted to the bottom of the housing, which in turn is fitted with a handle structure allowing the operator to operate and control the device 1 and read the display 69 of the voltmeter 4 while standing up at about 30 cm away from the sensing device.

Although the present invention has been described in the foregoing description by means of a preferred embodiment thereof, it can be modified at will and applied to various situations, within the scope of the appended claims without departing from the spirit and nature of the present invention. As an example, the resistance values of the resistors 22 and 32 (FIG. 1) can be adjusted to charge the central plate 4 and the side plates 5–8 (FIGS. 2 and 3) at the same rate when the electric field propagates in a given medium such as air. In the presence of a structure to be investigated, the charging rate of the central plate 4 will be affected by the local permittivity and the resulting voltage difference 76 (FIG. 5) will be detected through an amplifier-multiplier. An amplifier-multiplier should be used as the voltage difference 76 will be of lower amplitude whereby additional sensitivity is required.

I claim:

1. An electrostatic sensing device for investigating a surface and/or sub-surface structure presenting a permittivity to an electric field which is a function of at least one characteristic of said structure, comprising:

at least one first electrically conductive sensor plate that can be placed in the proximity of the structure under investigation, said first sensor plate comprising a first edge;

at least one second electrically conductive sensor plate comprising a second edge spaced apart from said first edge;

means for electrically charging said first and second plates at different rates, a charging rate of at least one of said first and second plates being affected by said permittivity of said structure to said electric field produced by said first and second plates being charged; and a detecting and generating circuit for detecting a difference between respective electric voltages on said first and second plates as said first and second plates charge, and for generating an output signal representative of an amplitude of said voltage difference which is affected by said charging rates of said first and second plates, said first and second plates being affected by said permittivity of the structure, whereby said output signal is a function of said permittivity and is therefore indicative of at least one characteristic of said structure under investigation;

wherein said detecting and generating circuit comprises:
a differential amplifier having a first input connected to said first plate and a second input connected to said second plate for amplifying said voltage difference between said first and second plates; and
a peak detector for detecting a highest amplitude of an amplified voltage difference from said differential amplifier and for generating said output signal in proportion to said highest amplitude.

2. An electrostatic sensing device as recited in claim 1, in which said plate charging means comprises means for adjusting the amplitude of said voltage to which the first and second plates are charged, and in which said first and second inputs of said differential amplifier are connected to said first and second plates through first and second voltage dividers, respectively.

3. An electrostatic sensing device as recited in claim 1, wherein said first and second inputs of said differential amplifier are connected to said first and second plates through first and second buffers, respectively.

4. An electrostatic sensing device as recited in claim 1, further comprising a voltmeter for displaying said highest amplitude of said output signal from said peak detector.

5. An electrostatic sensing device for investigating a surface and/or sub-surface structure presenting a permittivity to an electric field which is a function of at least one characteristic of said structure, comprising:

a central, electrically conductive planar sensor plate that can be placed in the proximity of said structure under investigation, said central plate comprising a first and second opposite edges;

first and second side electrically conductive sensor plates electrically interconnected and mounted adjacent to said first and second edges of said central plate, respectively, said first and second side plates comprising respective edges spaced apart from said first and second edges of said central plate, respectively, and each said first and said second side plates forming an acute angle with a plane of said central plate;

means for electrically charging said central plate and said interconnected first and second side plates at different rates, a charging rate of at least one of said central plate and said interconnected first and second side plates being affected by said permittivity of said structure to an electric field produced by said plates being charged; and a detecting and generating circuit for detecting a difference between electric voltages on said central plate and said interconnected first and second side plates as said plates charge, and for generating an output signal representative of an amplitude of said voltage difference which is affected by said charging rates of said central plate and said interconnected first and second side plates, which are affected by said permittivity of said structure, whereby said output signal is a function of said permittivity and is therefore indicative of said at least one characteristic of said structure under investigation;

wherein a spacing between a first edge of said central plate and said edge of said first side plate, a spacing between said second edge of said central plate and said edge of said second side plate, said acute angle between said central plate and said first side plate and said acute angle between said central plate and said second side plate are selected to focus said electric field produced by said central plate and said interconnected first and second side plates being charged, in said surface or sub-surface area of interest.

6. An electrostatic sensing device as recited in claim 5, wherein said plate charging means comprises means for charging said side plates at a rate higher than said charging rate of said central plate.

7. An electrostatic sensing device for investigating a surface and/or sub-surface structure presenting a permittivity to an electric field which is a function of at least one characteristic of said structure, comprising:

at least one first electrically conductive sensor plate that can be placed in the proximity of said structure under investigation, said first sensor plate being planar and comprising a first edge;

at least one second electrically conducively sensor plate comprising a second edge spaced apart from said first edge, said second sensor plate defining an acute angle with a plane of said first sensor plate;

means for electrically charging said first and second plates at different rates, said charging rate of at least one said first and second plates being affected by said permittivity of the structure to said electric field produced by said plates being charged; and detecting and generating circuit for detecting a difference between respective electric voltage on said first and second plates as said plates charge, and for generating an output signal representative of the amplitude of said voltage differences which is affected by said charging rates of said first and second plates which are affected by said permittivity of said structure, whereby said output signal is a function of said permittivity and is therefore indicatively of at least one characteristic of said structure under investigation; and means for adjusting a distance between said first and second edges and said acute angle of focus said electric field produced by said first and second sensor plates being charged, in said surface or sub-surface area of interest.

8. An electrostatic sensing device for investigating a surface and/or sub-surface structure presenting a permittivity to and electric field which is a function of at least one characteristic of said structure, comprising:

a central, electrically conductivity planar sensor plate that can be placed in the proximity of said structure under investigation, said central plate comprising three edges;

three side electrically conductive sensor plates electrically interconnected and mounted adjacent said three edges of said central plate, respectively, each of said three side plates comprising an edge spaced apart from said corresponding edge of said central plate and defining an acute angle with a plane of said central plate;

means for electrically charging said central plate and said interconnected three side plates at different rates, a charging rate of at least one of said central plate and said interconnected three side plates being affected by said permittivity of said structure of an electric field produced by said plates being charged; and a detecting and generating circuit for detecting a difference between respective electric voltages on said central plate and said interconnected three side plates as said plates charge, and for generating an output signal representative of said amplitude of said voltage difference which is affected by said charging rates of said central plate and said interconnected three side plates which are affected by said permittivity of said structure, whereby said output signal is a function of said permittivity and is therefore indicative of said at least one characteristic of said structure under investigation;

wherein a spacing between said edge of said side plate and a corresponding edge of said central plate, and said acute angle between each side plate and said central plate are selected to focus said electric field, produced by said central plate and said interconnected three side plates being charged, in said surface or sub-surface area of interest.

9. An electrostatic sensing device as recited in claim 8, wherein said plate charging means comprises means for charging said side plates at a rate higher than said charging rate of said central plate.

10. An electrostatic sensing device as recited in claim 8, in which said central plate comprises a fourth edge and said electrostatic sensing device comprises a fourth side electrically conductive sensor plate comprising an edge spaced apart from said fourth edge of said central plate and defining an acute angle with said plane of said central plate.

11. An electrostatic sensing device as recited in claim 10, wherein (a) said central plate is square, (b) said four edges of the central plate are straight and have given length, (c) said side plates are rectangular and elongated, and have a length equal to the length of said four edges of the central plate, and (d) each side plate is parallel to said corresponding edge to the central plate.

12. An electrostatic sensing device as recited in claim 10, further comprising switching means for disconnecting at least one of said four side plates from said three other side plates.

13. An electrostatic sensing device as recited in claim 10, wherein said plate charging means comprises means for charging the side plates at a rate higher than the charging rate of the central plate.

* * * * *